(12) United States Patent
Hamer et al.

(10) Patent No.: US 8,528,779 B2
(45) Date of Patent: Sep. 10, 2013

(54) DISPENSER WITH WASTE COLLECTION SPOOL, AND METHOD OF USING

(75) Inventors: Jeffrey L. Hamer, Springville, IN (US); Ken F. Teeters, Zionsville, IN (US); Ravi Thomas, Avon, IN (US); Andrew Linton, Woodthorpe (GB); Tim Stern, Belper (GB); Mark White, Doncaster (GB)

(73) Assignee: 3M Innovative Properties Company, St. Paul, MN (US)

( * ) Notice: Subject to any disclaimer, the term of this patent is extended or adjusted under 35 U.S.C. 154(b) by 242 days.

(21) Appl. No.: 12/913,417

(22) Filed: Oct. 27, 2010

(65) Prior Publication Data

US 2012/0104014 A1 May 3, 2012

(51) Int. Cl.
*B65D 83/00* (2006.01)
*B65H 1/00* (2006.01)

(52) U.S. Cl.
USPC .......................................................... 221/71

(58) Field of Classification Search
USPC ............... 221/25, 69–72, 155, 191, 194, 197, 221/208, 239, 255, 256, 297
See application file for complete search history.

(56) References Cited

U.S. PATENT DOCUMENTS

| | | | | | |
|---|---|---|---|---|---|
| 2,465,876 | A | * | 3/1949 | Hornung | 221/72 |
| 2,860,941 | A | * | 11/1958 | Fromwiller | 312/36 |
| 3,729,892 | A | * | 5/1973 | Aslund et al. | 53/399 |
| 5,065,894 | A | * | 11/1991 | Garland | 221/25 |
| 6,003,722 | A | * | 12/1999 | Thurner | 221/25 |
| 6,962,266 | B2 | * | 11/2005 | Morgan et al. | 221/25 |
| 2005/0154491 | A1 | * | 7/2005 | Anderson et al. | 700/236 |
| 2009/0218364 | A1 | | 9/2009 | Bizzell | |
| 2010/0018987 | A1 | | 1/2010 | Hamer | |

OTHER PUBLICATIONS

International Search Report, PCT/US2011/057588, mailed May 22, 2012, 4 pages.

* cited by examiner

*Primary Examiner* — Gene Crawford
*Assistant Examiner* — Kevin L Randall, Jr.
(74) *Attorney, Agent, or Firm* — Kenneth B. Wood

(57) ABSTRACT

Herein are disclosed methods for liberating one or more packaged devices from a packaging web, and a dispenser for performing such methods. The packaging web is separated into first and second waste webs which are co-wound onto a common collection spool.

28 Claims, 7 Drawing Sheets

DISPENSER WITH WASTE COLLECTION SPOOL, AND METHOD OF USING

BACKGROUND

Safety protection devices, such as earplugs, are routinely used in consumer, commercial, and industrial environments. Often, such devices are distributed in large volumes to a substantial number of users. Dispensers may be used for such purposes.

SUMMARY

Herein are disclosed methods for liberating one or more packaged devices from a packaging web, and a dispenser for performing such methods. The packaging web is separated into first and second waste webs which are co-wound onto a common collection spool.

In one aspect, herein is disclosed a dispenser configured to liberate at least one packaged device from a packaging web that is separable into first and second waste webs and that contains a plurality of packaged devices, the dispenser comprising: a packaging web path along which the packaging web is conveyed to a web-separation point at which the packaging web is separated into first and second waste webs with at least one device being liberated from the packaging web by the act of separating the packaging web into first and second waste webs; a device receptacle configured to receive the liberated device; a first waste web path along which the first waste web is conveyed to a collection spool; and, a second waste web path along which the second waste web is conveyed to the collection spool; the collection spool being configured so that the first and second waste webs can be co-wound on the collection spool to form a co-wound waste roll.

In another aspect, herein is disclosed a method of liberating at least one packaged device from a packaging web that is separable into first and second waste webs and that contains a plurality of packaged devices, the method comprising: conveying the packaging web along a packaging web path to a web-separation point at which the packaging web is separated into first and second waste webs with at least one device being liberated from the packaging web by the act of separating the packaging web into first and second waste webs; allowing the liberated device to fall into a device receptacle from which it may be retrieved by a user; conveying the first waste web along a first waste web path to a collection spool; conveying the second waste web along a second waste web path to the collection spool; and, co-winding the first and second waste webs on the collection spool.

These and other aspects of the invention will be apparent from the detailed description below. In no event, however, should the above summaries be construed as limitations on the claimed subject matter, which subject matter is defined solely by the attached claims, as may be amended during prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

Figure 1:
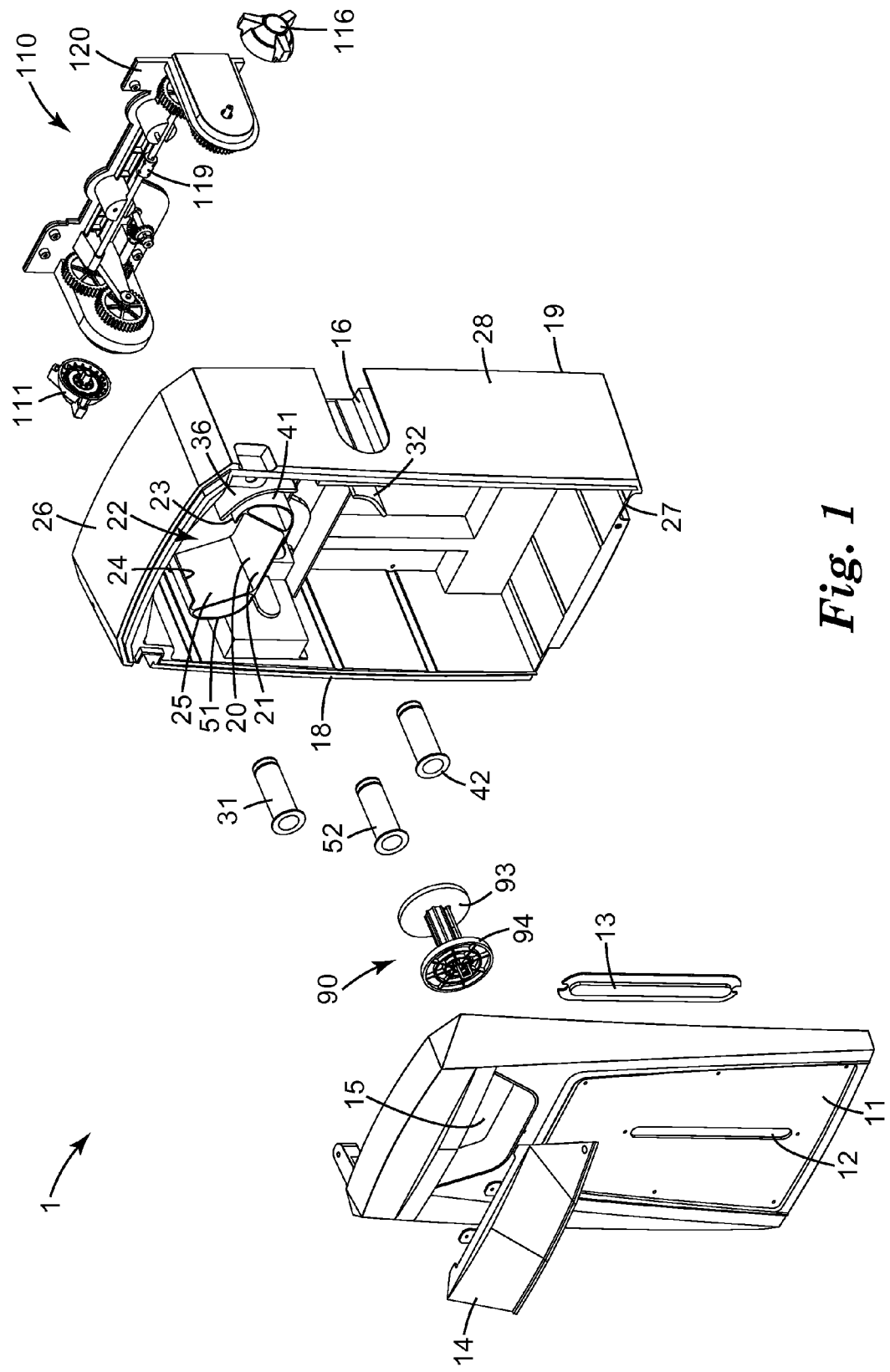
FIG. 1 is a side perspective, partially exploded view of an exemplary dispenser as disclosed herein.
Figure 2:
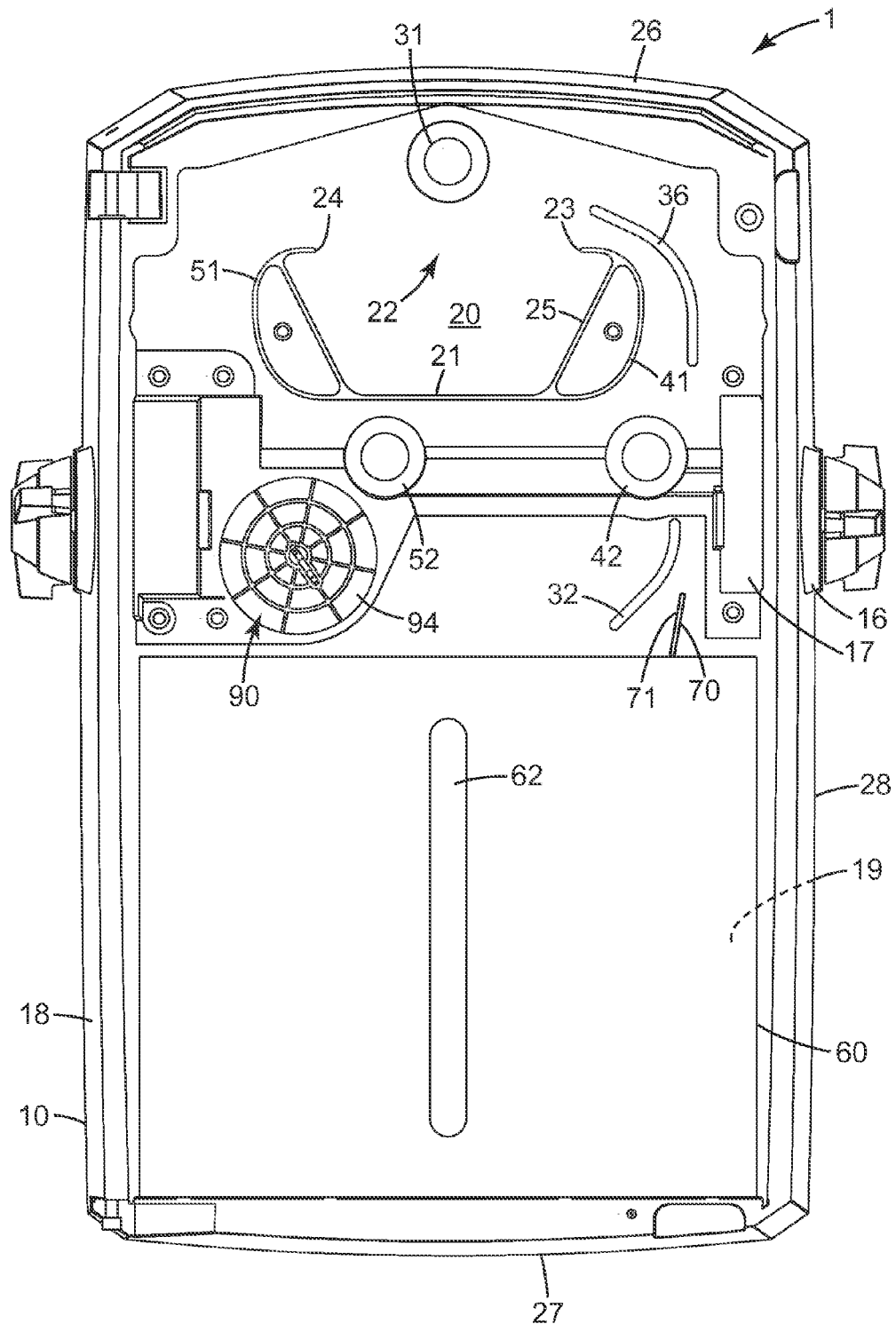
FIG. 2 is front view of the dispenser of FIG. 1, with the front cover removed.

Shown in FIG. 1 in partially exploded side perspective view, and in FIG. 2 in front view with the front cover removed, is an exemplary dispenser 1. Exemplary dispenser 1 comprises housing 10 comprising a first major (front) side comprising front cover 11, back side 19, first minor side 18, second minor side 28, top 26, and bottom 27. Front cover 11 may comprise an opening 15 through which dispensed devices 80 may be retrieved. Shield 14 may be provided, which may be particularly useful if dispenser 1 is used outdoors. Front cover 11 may be removable so as to allow access to the interior of dispenser 1, e.g. in order to position cartridge 60 in dispenser 1 as shown in FIG. 2. Front cover 11 may comprise opening 12 that may comprise transparent window 13, and may be aligned with an opening in cartridge 60 to allow visual interrogation of the interior of cartridge 60, as discussed later herein.

Figure 3:
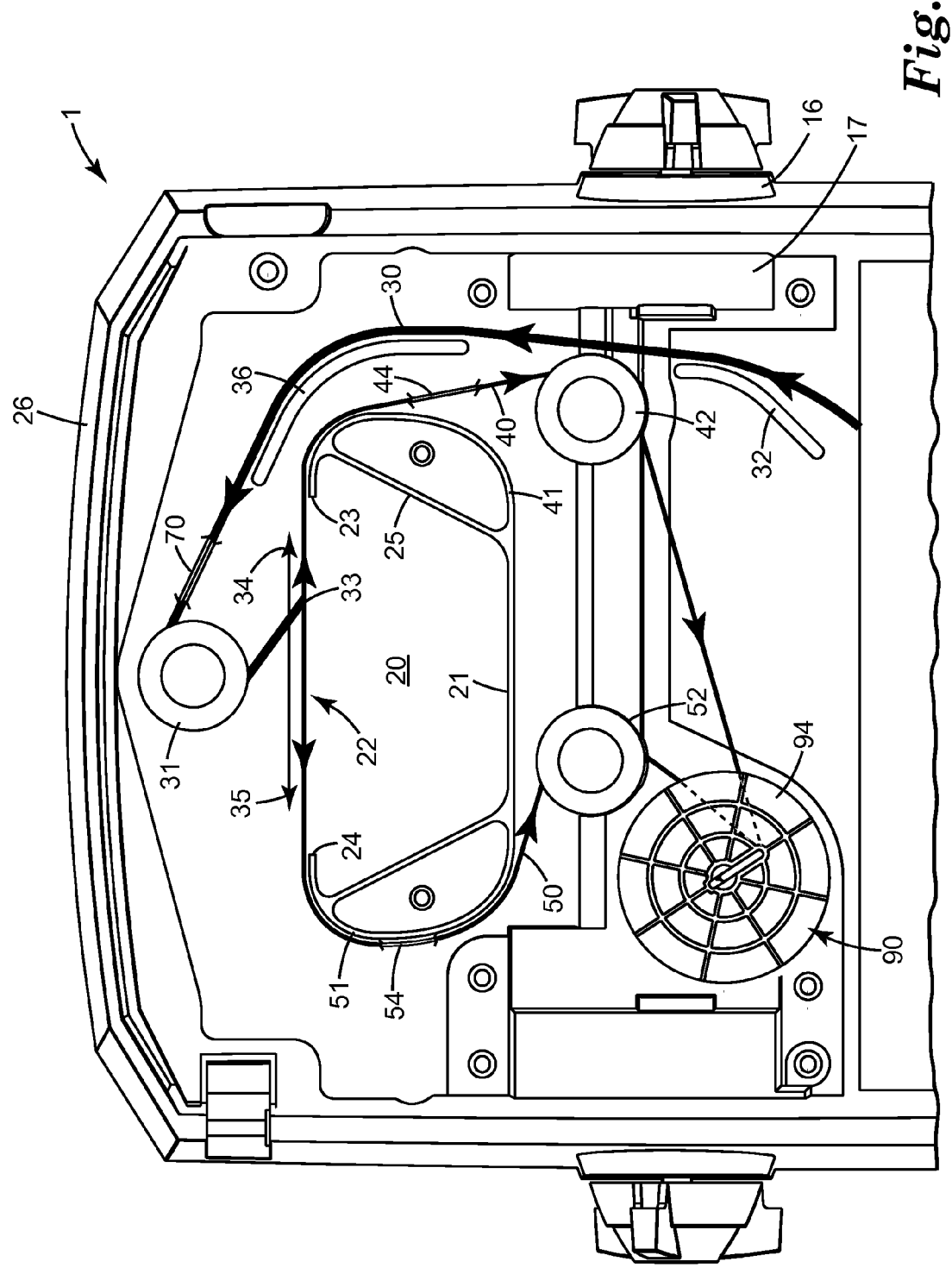
FIG. 3 is an enlarged view of the web-path-containing portion of the dispenser of FIG. 2.

Dispenser 1 is configured to process packaging web 70 and to liberate one or more packaged devices 80 therefrom. As shown in FIG. 3, dispenser 1 comprises packaging web path 30 along which packaging web 70 may be conveyed (e.g., from cartridge 60) to web-separation point 33. By web-separation point is meant a location within the interior of dispenser 1 at which packaging web 70 is physically separated into a first waste web 44 and a second waste web 54 with device 80 being liberated from packaging web 70 by the act of separating packaging web 70 into first and second waste webs. Web-separation point 33 is located vertically above some portion of opening 22 of device receptacle 20, so that liberated device 80 may fall under the influence of gravity through opening 22 into device receptacle 20, from which it may be retrieved. (As used herein, the term vertical refers to a direction extending between the top and bottom of dispenser 1, and will be generally aligned with the Earth's gravity in customary use of dispenser 1. The phrase vertically above denotes generally toward top 26 of dispenser 1 along the vertical direction). Device 80 may fall onto floor 21 of device receptacle 20 or may be caught (e.g., by the hand of a user) before contacting floor 21. Spars 25 may be provided so as to reinforce device receptacle 20 and/or to direct device 80 generally towards the lateral center of receptacle 20. (As used herein, the term lateral signifies a direction extending generally between minor sides 18 and 28 of dispenser 1. In customary use of dispenser 1, a lateral direction will be generally orthogonal to gravity).

Figure 4:
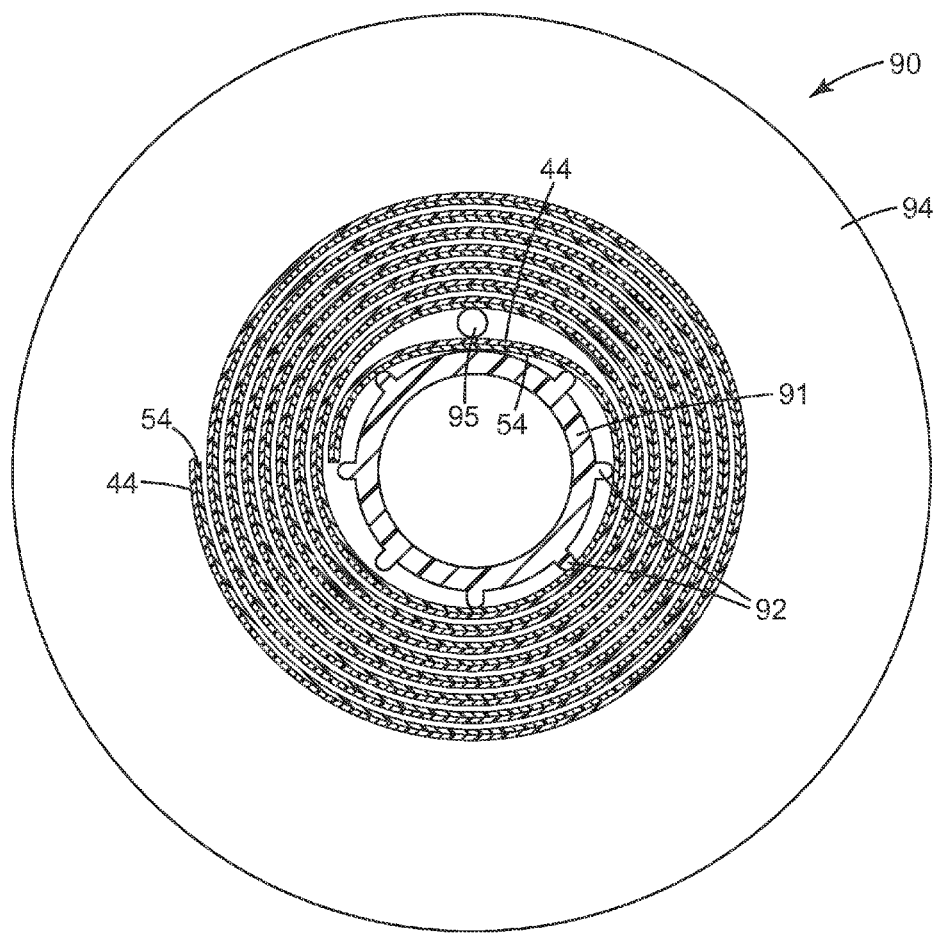
FIG. 4 is a side cross sectional view of an exemplary waste web collection spool containing a co-wound waste web.

Dispenser 1 further comprises first waste web path 40 along which first waste web 44 may be conveyed to waste web collection spool 90. Dispenser 1 also comprises second waste web path 50 along which second waste web 54 may be conveyed to waste web collection spool 90. First waste web 44 and second waste web 54 are co-wound into collection spool 90, meaning that the two webs are both wound onto collection spool 90 so as to form a single waste roll 77 with at least one of the waste webs being in substantially overlapping configuration with the other waste web and with a major surface of one of the webs being in substantial contact with a major surface of the other waste web (e.g., as shown in FIG. 4).

Thus, in use of dispenser 1, packaging web 70 is separated into first and second waste webs 44 and 54 (with concomitant liberation of device 80 from packaging web 70) that are then conveyed through separate paths to be co-wound onto collection spool 90 to form a single waste web roll 77 that contains both waste web 44 and waste web 54. Such winding of multiple waste webs onto a common spool may have advantages over the winding of waste webs onto separate spools as disclosed for example in U.S. Patent Application Publication 2010/0018987 to Hamer. However, it has been found that the co-winding first and second waste webs onto a common spool may cause web separation point 33 to move somewhat upon continued or successive use of dispenser 1, owing to the slight asymmetry that is inherent in the co-winding of separate webs onto a common spool. Nonetheless, the discoveries presented herein enable successful functioning of a dispenser comprising a common waste web spool.

For example, with reference to FIG. 3, dispenser 1 may be configured so that upon initially threading a leader portion (i.e. a portion not containing packaged devices 80) of packaging web 70 into packaging web path 30 and separating (e.g., splitting) the leader portion into waste webs 44 and 54 that are respectively threaded into first waste web path 40 and second waste web path 50 and that are secured to collection spool 90, web-separation point 33 is located at an initial position 34 that is adjacent an edge (in the case of FIG. 3, right edge 23) of opening 22 of device receptacle 20. Initial position 34 may be chosen to be close to edge 23, but not so close that edge 23 might interfere with the ability of liberated device 80 to fall through opening 22. Continued use of dispenser 1 (i.e., continued co-winding of waste webs 44 and 54 onto spool 90), whether continuously or in an intermittent manner, may result in web separation point 33 gradually traversing laterally over (across) opening 22 (e.g., along the path marked by the double-headed arrow in FIG. 3) until (when packaging web 70 is exhausted) web-separation point 33 reaches a final position 35 that is proximate the other edge (in this case, left edge 24) of opening 22. Careful design of the geometries and lengths of the various web paths, of packaging web 70, and of opening 22, can provide that final position 35 is not unacceptably close to the edge of opening 24. Thus, in some embodiments dispenser 1 may comprise a web-separation point that is a traveling web-separation point, meaning that the web-separation point is not fixed in space but rather traverses a distance in the course of continued operation of the dispenser (whether such operation is continuous or intermittent).

In some embodiments, at web-separation point 33 first waste web path 40 and second waste web path 50 may be oriented generally opposite each other (e.g., as shown in FIG. 3). That is, at the web-separation point 33 first waste web 44 may be motivated to move generally in a first direction, and second waste web 54 may be motivated to move in a second direction that is generally opposite that of first waste web 44. Both directions may be generally lateral (as defined earlier herein) with respect to dispenser 1. In such a case, separating packaging web 70 into first and second waste webs 44 and 54 may cause device 80 to be liberated from packaging web so as to fall (i.e., vertically downward) in a direction substantially orthogonal to the directions of motion of first and second waste webs 44 and 54 at web-separation point 33.

In some embodiments, web-separation point 33 may be a floating web-separation point, meaning that web-separation point 33 is at a location that is unoccupied except for webs 70, 44 and 54 themselves and that is not proximate a gap between a pair of closely spaced rollers (in this context, the term proximate means within 2 cm of, and the term closely spaced rollers means rollers whose surfaces are within 5 mm of each other at their point of closest approach). Such a floating web-separation point may be contrasted with a web-separation point that is defined by one or more rollers which a packaging web traverses as it is separated into waste webs, and may be particularly contrasted with a web-separation point that is defined by a pair of closely-spaced rollers between which the packaging web traverses as it enters the web-separation point. Such a floating web-separation point may be still further contrasted with a pair of closely spaced rollers that are used to motivate a packaging web into the web-separation point. It has been discovered that it is not necessary to provide such rollers at the web-separation point; in fact, such rollers might render it difficult to use a traveling web-separation point as disclosed above.

With further reference to FIG. 3, in some embodiments packaging web path 30 may be at least partially defined by at least a first packaging web guiding vane 32. By vane (in this and all other occurrences herein) is meant a non-moving member that has at least one surface configured to allow a web to slidably traverse at least a portion thereof and that may be molded as part of housing 10, may be a separate piece attached thereto, etc. Packaging web guiding vane 32 comprises a laterally outward-facing surface of which is configured to allow packaging web 70 to slidably traverse at least a portion thereof (As used herein, the terms outward and outwardly-facing, when used with respect to a component in the interior of dispenser 1, means generally toward the portion of dispenser housing 10 that is closest to the component. The term laterally outwardly facing as used with respect to a component in the interior of dispenser 1 means facing toward a minor surface of dispenser housing 10 to which the component is closest.) In addition, at least a portion of packaging web guiding vane 32 may be configured to prevent contact between at least a portion of packaging web 70 and at least a portion of a waste web (e.g., waste web 44). Packaging web path 30 may be further defined by a second guiding vane 36, a laterally outward-facing surface of which is configured to allow packaging web 70 to slidably traverse at least a portion thereof. In addition, at least a portion of second guiding vane 36 may be configured to prevent contact between at least a portion of packaging web 70 and at least a portion of a waste web, in similar manner as for vane 32.

In some embodiments, packaging web path 30 may be at least partially defined by at least one packaging web guiding roller 31, as shown in exemplary manner in FIG. 3. Roller 31 may be located generally vertically above device receptacle 20 and may change the direction of movement of packaging web 70 (i.e., may change the direction of packaging web path 30). In various embodiments, roller 31 may change the direction of movement of packaging web 70 by at least about 30, 50, 70, 90, or 110 degrees or more. (In view the above discussions, it will be appreciated that the amount to which roller 31 may change the direction of packaging web path 30 may depend on the location of web-separation point 33 and thus may change during continued operation of dispenser 1). With respect to this and all other uses of the term roller herein, while the term roller is used for convenience, it has been found that such rollers do not necessarily need to be rotatably mounted within dispenser 1, although this can be done if desired. As such, terms such as rollers and vanes are used herein merely for convenience of description and there may be no firm dividing line between the aforementioned guiding vanes, and guiding rollers (although in general such rollers may be distinguished from vanes by way of having a smaller radius of curvature). Such rollers and/or vanes may be molded directly into housing 10 of dispenser 1. However, (e.g. if it is desired to provide flanges at a longitudinal end of a roller that is distal from an end at which the roller is connected to housing 10, for enhanced guiding of a web), it may be convenient to provide rollers as separate pieces (as in the exemplary embodiment of FIGS. 1-3) rather than being molded directly into housing 10.

In some embodiments, first waste web path 40 may be at least partially defined by at least a first waste web guiding vane 41, a laterally outward-facing surface of which is configured to allow first waste web 40 to slidably traverse at least a portion thereof. In some embodiments, guiding vane 41 may comprise a generally arcuate structure that at least partially defines a portion (e.g., a side portion) of device receptacle 20. In some embodiments, first waste web path 40 may be at least partially defined by at least a first waste web guiding roller 42, which may change the direction of motion of first waste web 44 (i.e., may change the direction of first waste web path 40), e.g. by at least about 30, 50, 70, or 90 degrees or more.

In some embodiments, second waste web path 50 may be at least partially defined by at least a second waste web guiding vane 51, a laterally outward-facing surface of which is configured to allow second waste web 54 to slidably traverse at least a portion thereof. In some embodiments, guiding vane 51 may comprise a generally arcuate structure that at least partially defines a portion (e.g., a side portion) of device receptacle 20. In some embodiments, second waste web path 50 may be at least partially defined by at least a second waste web guiding roller 52, which may change the direction of second waste web path 50, e.g. by at least about 30, 50, 70, 90, or 110 degrees or more. In some embodiments, the amount to which second waste web guiding roller 52 changes the direction of second waste web path 50 will be different from, e.g. greater than, the amount to which first waste web guiding roller 42 changes the direction of first waste web path 40.

Additional guiding rollers and/or guiding vanes may be provided in any of packaging web path 30 and first and second waste web paths 40 and 50, if desired.

In some embodiments, the length of first waste web path 40 (i.e., from web-separation point 33 to collection spool 90) may be similar to that of second waste web path 50. In this context similar means that the length of first waste web path 40 is from about 70% of, to about 130% of, the length of second waste web path 50. It will be appreciated that the use of a traveling web-separation point as disclosed above, may cause the length of one or both of waste web paths 40 and 50 to change with continued use of dispenser 1.

First and second waste web paths 40 and 50 converge and meet at waste web collection spool 90, which is shown in exemplary embodiment in FIGS. 1, 4, 5 and 6. Collection spool 90 may comprise core 91, which may comprise ribs 92 (which may e.g. aid in the capturing and initial co-winding of waste webs 44 and 54 onto spool 90), and may further comprise flanges 93 and 94. Collection spool 90 may comprise holding rod 95 that establishes a narrow gap between holding rod 95 and core 91 through which leader ends of waste webs 44 and 54 may be inserted in order to initially capture the waste webs onto core 91. Collection spool 90 may further comprise at least one gear (not shown in any figure) that mates with a gear of drivetrain 110 in order that collection spool 90 may be motivated to rotate, as discussed later herein.

In operation of dispenser 1, first and second waste webs 44 and 54 are co-wound onto collection spool 90 to form a single waste roll 77 that contains both waste web 44 and waste web 54, as shown in FIG. 4. Upon the exhaustion of a supply of packaging web 70 (e.g., as provided in a cartridge 60), it may be necessary to remove waste roll 77 from collection spool 90. This may advantageously be done by sliding waste roll 77 off of core 91 in a direction generally aligned with the longitudinal axis of core 91. In order that this be accomplished, at least one of flanges 93 or 94 may be detachable from core 91. Moreover, holding rod 95 (which is not limited to a cylindrical geometry) may be designed so that it may be partially or completely removed from collection spool 90. It has been found that this may sufficiently reduce the force with which waste roll 77 is held on collection spool 90 to facilitate the slidable removal of waste roll 77 from core 91. Thus, in some embodiments, holding rod 95 may comprise a securing mechanism that allows holding rod 95 to be secured in place on collection spool 90 and that allows holding rod 95 to be unsecured when desired. Any suitable securing mechanism can be used.

Figure 5:
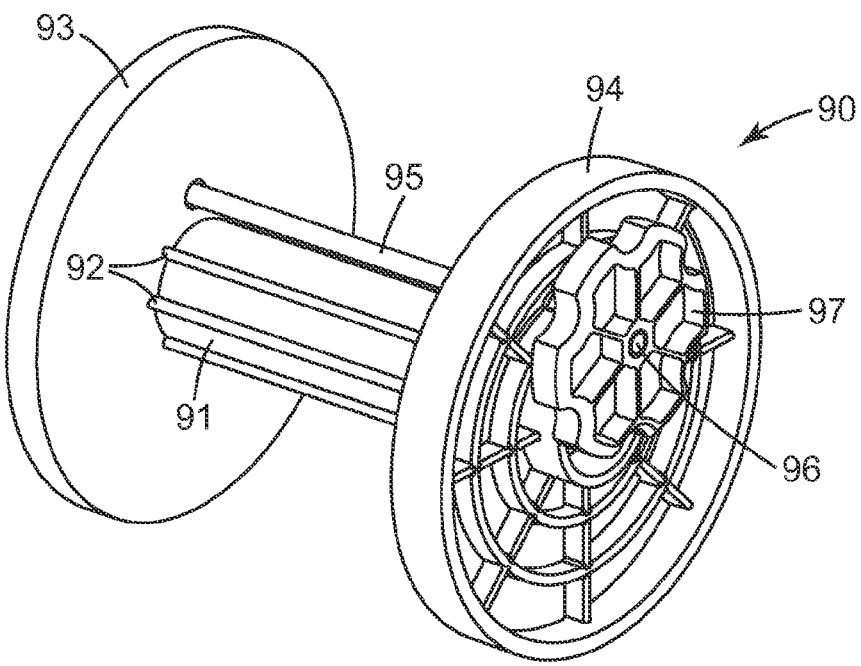
FIG. 5 is a side perspective view of a waste web collection spool with a holding rod with an exemplary securing mechanism.

One such exemplary securing mechanism is shown in FIG. 5. In such a case, holding rod 95 may have a threaded end 96 that protrudes through a through-hole in flange 94 and to which a threaded nut 97 can be attached. Nut 97 can thus be detached from holding rod 95 in order to allow holding rod 95 to be at least partially slidably removed to facilitate (in combination with removal of flange 93) slidable removal of waste roll 77. Alternatively, protruding end of holding rod 95 may contain a through-hole through which a cotter pin can be inserted and removed when desired. Any other suitable securing mechanism, relying on one or more clips, fasteners, and the like, may be used.

It has also been found that it may not be necessary to completely remove holding rod 95, or to partially move it in a direction aligned with the longitudinal axis of core 91, in order to facilitate slidable removal of waste roll 77. Rather, it has been found that moving holding rod 95 slightly radially inward toward core 91 may sufficiently reduce the force with which waste roll 77 is held on collection spool 90 to facilitate the slidable removal of waste roll 77 from core 91. Thus, in some embodiments holding rod 95 may be configured so as to be securable in a first position, and to be unsecured and then at least a portion of holding rod 95 moved at least slightly radially toward core 91. This may be achieved e.g. by an arrangement of the general type shown in exemplary manner in FIG. 6. In such case, an end of holding rod 95 may protrude through a through-hole 99 in flange 94 that takes the form of a radially-oriented slot. Slot 99 may be configured so that holding rod 95 can be secured in the radially outermost portion of the slot, and then can be unsecured and moved radially inward when it is desired to remove waste roll 77. Holding rod 95 may comprise enlarged head piece 98 to facilitate such operation, as shown in the exemplary embodiment of FIG. 6. Enlarged head piece 98 may reside in an enlarged, radially outward portion of keyhole-shaped slot 99, thus preventing holding rod 95 from moving radially toward core 91. At a desired time, enlarged head piece 98 may be pulled outward (along the longitudinal axis of core 91) so that at least the portion of holding rod 95 nearest to flange 94 can be moved radially toward core 91 (e.g., into the narrower portion of keyhole-shaped slot 99), thus loosening holding rod 95 to facilitate (in combination with removal of flange 93) removal of waste roll 77 from core 91.

Other arrangements are possible. For example, a portion, or all, of collection spool 90 may be disposable so as to be discarded along with waste roll 77.

Figure 6:
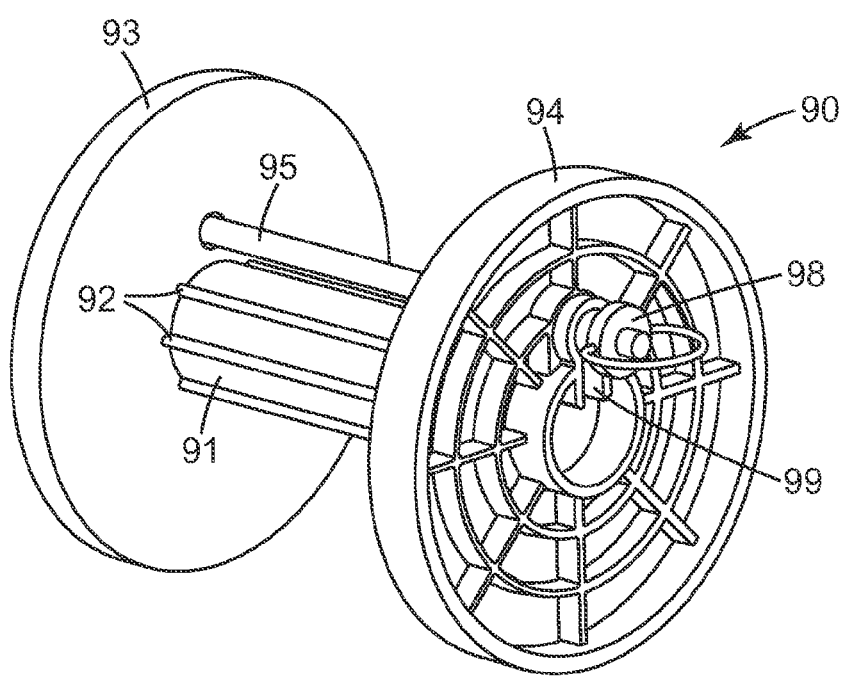
FIG. 6 is a side perspective view of a waste web collection spool with a holding rod with another exemplary securing mechanism.
Figure 7:
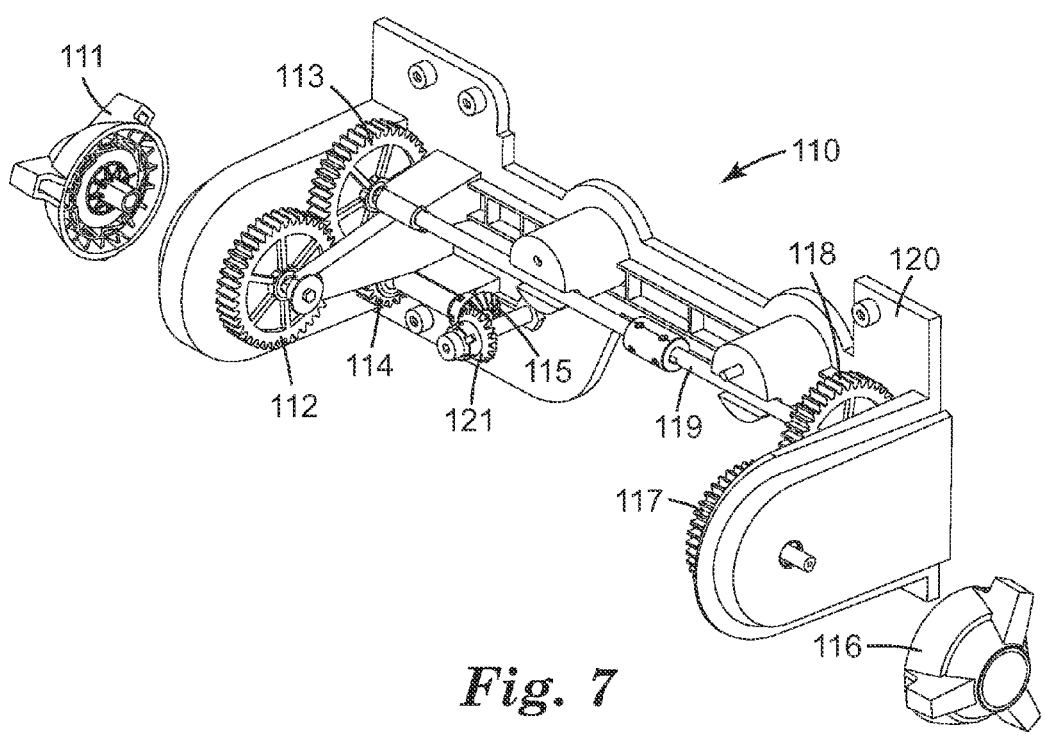
FIG. 7 is a side perspective, partially exploded view of an exemplary drivetrain.

Dispenser 1 may comprise a drivetrain as shown in exemplary embodiment FIG. 1 and in further detail in FIG. 6. In general, such a drivetrain serves to motivate collection spool 90 to rotate, which co-winds waste webs 44 and 54 onto spool 90, pulls waste webs 44 and 54 along waste web paths 40 and 50 respectively, pulls packaging web 70 along packaging web path 30, and removes additional packaging web 70 from cartridge 60. In such embodiments, collection spool 90 may be the only component of the web paths that is actively driven. In other embodiments, the drivetrain may be configured such that other components (e.g., rollers) are also actively driven. In some embodiments, such a drivetrain may be as simple as a rod that is connected to collection spool 90 and that is directly connected to an external actuator (e.g., handle) that is located outside of housing 10 of dispenser 1. In such case movement (e.g., rotation) of the external actuator can directly cause rotation of collection spool 90. Such a configuration, however, might necessitate placing the actuator on the front side (e.g., outside of front cover 11) of dispenser 1. In some cases it may be advantageous to provide an actuator on a minor side of dispenser 1. In such case, a drivetrain such as the exemplary drivetrain 110 of FIGS. 1 and 6 may be used. Drivetrain 110 comprises a first external actuator (e.g., handle) 111 that is positioned outwardly adjacent minor side 18 of dispenser housing 10 and that is connected to planetary gears 112, 113, and 114, at least one of which is connected to bevel (e.g., miter) gear 115 that is configured to drive bevel gear 121 that is configured to rotate collection spool 90. (Such bevel gears may be needed in this instance since the axis of rotation of actuator 111 is orthogonal to the axis of rotation of collection spool 90).

In some cases it may be advantageous to provide a second actuator 116 that is positioned outwardly adjacent second minor side 28 of dispenser housing and that is connected to drivetrain 110 via planetary gears 117 and 118 and driveshaft 119. Such an arrangement allows dispenser 1 to be operated by the actuation of either, or both, of actuators 111 and 116.

First and/or second actuators 111 and 116 can be provided with a one-way braking mechanism to prevent them from being actuated in the wrong direction (e.g., rotated in the wrong direction), or a clutch mechanism that may allow such actuation but will disengage the actuator from drivetrain 110. Such provisions may minimize the chance of inadvertent motivation of collection spool 90, and of the various webs, to move in an undesired direction.

In the exemplary embodiments discussed herein, rotational actuation has been discussed. However, any convenient mode of actuation, whether rotational, rectilinear, etc., may be used, using any suitable type of actuator (handle) and mechanism. In the exemplary embodiments discussed herein, manual actuation (e.g., by the hand of a user) has been discussed. However, any convenient method of actuation can be used, such as facilitated by an electrically operated motor. In such case, actuation may be initiated by any suitable button, level, switch, knob, motion sensor and the like.

Drivetrain 110 may be conveniently provided as a modular unit supported by molded assembly 120 and which may be inserted into receiving slots 16 of dispenser housing 10. Such an arrangement may provide for easy servicing of drivetrain 110 and may also allow many of the components of drivetrain 110 to be shielded behind drivetrain covers 17.

In some embodiments, packaging web 70 may be provided within dispenser 1 without residing in any type of container other than dispenser housing 10 itself. In other embodiments, packaging web 70 may be provided in cartridge 60, as shown in exemplary manner in FIGS. 2 and 8. Cartridge 60 may be sized and shaped to fit into a portion, e.g. a lower interior portion, of dispenser 1. Cartridge 60 may be made of any suitable material, e.g. plastic, cardboard, and the like. Cartridge 60 may contain one or more packaging webs 70. In some embodiments, cartridge 60 may contain one packaging web 70; in such case waste collection spool 90 may be designed to accommodate a larger quantity of co-wound waste webs than corresponds to the length of packaging web 70 contained in cartridge 60. Such an arrangement may ensure that collection spool 90 is not filled to capacity prior to the exhaustion of packaging web 70.

Cartridge 60 may comprise opening 61 (which may be, e.g., a knockout opening in cardboard cartridge 60) through which packaging web 70 may be removed. Cartridge 60 may further comprise opening 62 (which may also be a knockout opening) which may allow visual determination of the amount of packaging web remaining in cartridge 60. Opening 62 may be aligned with opening 12 of dispenser housing 10, as mentioned previously.

As discussed herein, dispenser 1 is configured to process packaging web 70 and to liberate packaged devices 80 therefrom. By web is meant a continuous, elongated strip of material that is at least 1 meter long in the longitudinal direction of the web. By packaging web is meant a web containing a plurality of devices that are in spaced relation along the longitudinal dimension of web. In further detail, packaging web 70 may be formed from an elongated continuous plastic sleeve, such as may be achieved e.g. by bringing together the longitudinal edges of a continuous plastic film and bonding the edges to each other (e.g. by heat sealing, by adhesive bonding, or the like). Devices 80 may be positioned at desired intervals within the longitudinal length of the sleeve and at least one seal applied between successive devices 80 such that packaging web 70 takes the form of a continuous succession of pouches each of which contains a device 80. (While for convenience each pouch is described in exemplary manner herein as containing one device 80, if desired each pouch can contain multiple devices 80, with the devices 80 in each pouch being identical to each other, or being different from each other). When viewed in cross section, packaging web 70 may comprise an upper film and a lower film (both of which may be obtained from the same precursor film, e.g. by joining the edges of the precursor film together as described above), with devices 80 contained therebetween.

Packaging web 70 is separable into waste webs 44 and 54. In some embodiments, packaging web 70 may comprise one or more lines of weakness that are oriented generally down the longitudinal length of packaging web 70 and that can enhance the separating of packaging web 70 into first and second waste webs. Such lines of weakness may be achieved e.g. by partial or complete perforation of the film comprising packaging web 70, e.g. by mechanical means, by laser perforation, and so on. In particular embodiments, two such lines of weakness may be provided, one in an upper film of packaging web 70 and one in a lower film of packaging web 70, so as to further enhance the ability of packaging web 70 to be torn and separated. In specific embodiments, the lines of weakness may be provided such that packaging web 70 may be separable into waste webs 44 and 54 that are similar in width.

It will be appreciated that it may not necessary to separate packaging web 70 in the particular manner described above. For example, in some embodiments, web 70 may comprise upper and lower films that are peelably separable from each other. This may be provided e.g. by bonding the films to each other (e.g., along their longitudinal edges, and intermittently across the width of the films, in order to form pouches) in a manner that permits the films to be separated from each other.

In various embodiments, packaging web 70 may be e.g. from a few tens of meters long, up to one hundred meters or more. In such embodiments, packaging web 70 may comprise e.g. from a few dozen devices 80 to a few hundred or more devices 80. The downweb spacing between devices 80 (or between groups of devices, if multiple devices are present in each pouch of packaging web 70), may be chosen as desired. In various embodiments, the spacing may be at least 5, 10, or 15 centimeters. In further embodiments, the spacing may be at most 40, 30 or 20 centimeters. The number of devices 80 in a packaging web 70, the spacing therebetween, etc., may of course be chosen in view of the size and shape of the particular device 80.

Packaging webs that may be suitable for use herein are described in further detail in U.S. Patent Application Publication 2010/0018987 to Hamer, which is incorporated by reference in its entirety herein.

Packaging web 70 may comprise a leader portion 71 which may comprise a portion of web 70 (e.g., positioned closest to opening 61 of cartridge 60 as initially supplied) that does not comprise devices 80. Leader portion 71 may comprise a leading (terminal) end 72, and a trailing end 73 opposite the leading end, with trailing end 73 being the end adjacent the device-containing portion of packaging web 70. Use of leader portion 71 may provide that devices 80 are not unwantedly liberated from packaging web 70 in the act of initially threading web 70 through the web paths of dispenser 1. In aid of this, leader portion 71 of packaging web 70 may be e.g. at least as long as the length of first waste web path 40. Leader portion 71 may be provided e.g. by attaching (e.g. splicing) a length of film to a terminal end of packaging web 70; or, it may be provided by simply not loading devices 80 into a certain number of pouches nearest the leading end of packaging web 70. If desired, indicia, instructions, etc. may be provided (e.g., printed) onto leader portion 71 to facilitate the threading of leader portion 71 into the web paths of dispenser 1.

In some embodiments, leader portion 71 may comprise a line of weakness (i.e., oriented generally along the longitudinal direction of leader portion 71), in order to facilitate the separating (i.e., splitting) of leader portion 71 into first and second sections (i.e., first and second waste webs) and the threading of the first and section sections into the above-described web paths. In some embodiments, leader portion 71 may be pre-split (e.g., along at least a portion of its longitudinal length) into first and second sections, so that leader portion 71 does not need to be manually split by a user in the process of threading web 70 into the web paths of dispenser 1. In further embodiments, the longitudinal length of the pre-split sections of leader portion 71 may be chosen so that, when the terminal (leading) ends of the pre-split portions are secured to collection spool 90 and each of the pre-split leader sections is threaded into its respective web path, web-separation point 33 is positioned at initial position 34 as discussed earlier herein. In such embodiments, the initial length of first waste web path 40 and second waste web path 50 (each as measured from web-separation point 33 at initial position 34, to collection spool 90) may be substantially identical (e.g., within about 5% of each other).

Figure 8:
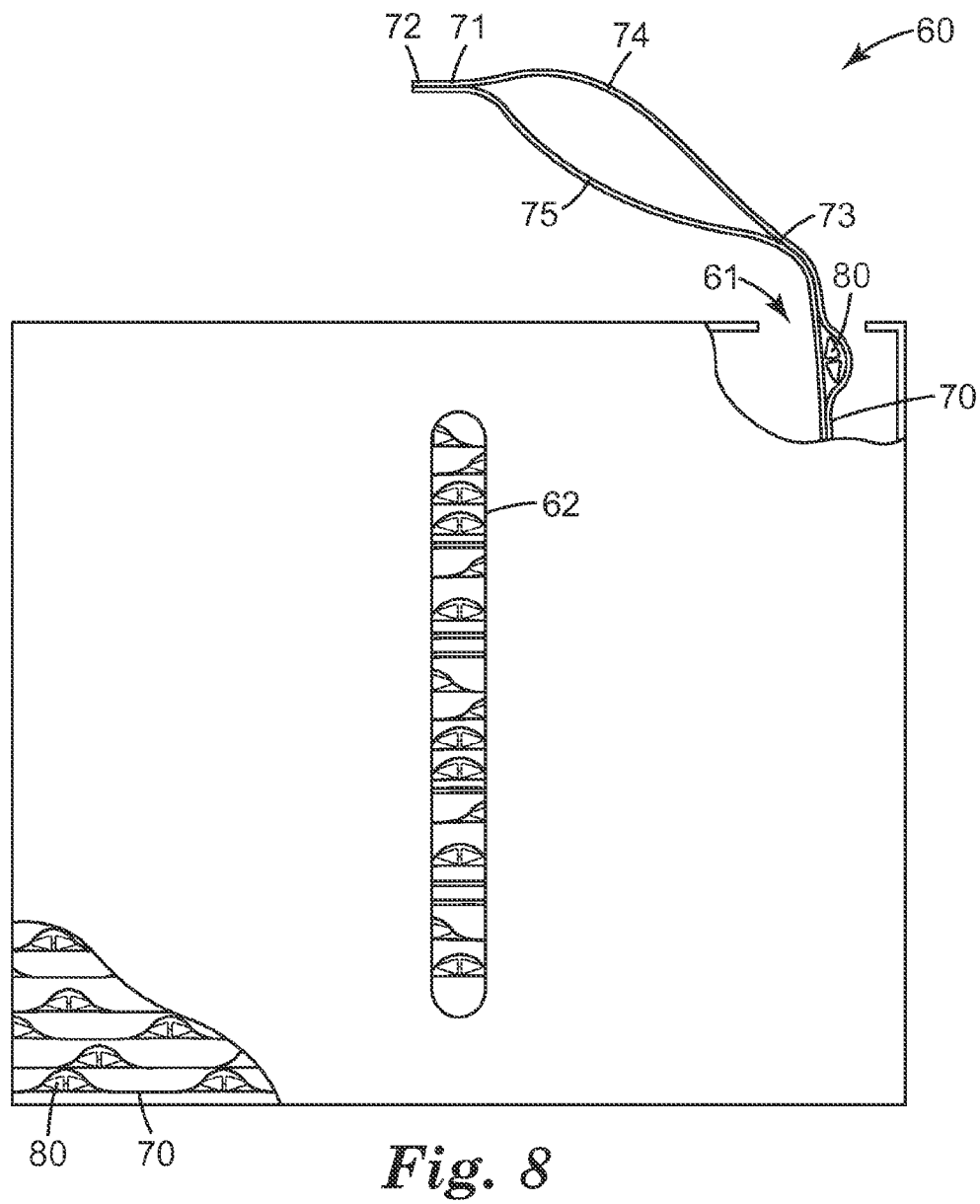
FIG. 8. is a front view, in partial cutaway, of an exemplary cartridge and packaging web.

In particular embodiments of the type shown in exemplary manner in FIG. 8, leader portion 71 may be pre-split into first and second sections 74 and 75 over a portion of its longitudinal length, but may be a single (unsplit) web at its terminal (leading) end 72. (This may be achieved by not pre-splitting the leading end of leader portion 71; or, by pre-splitting leader portion 71 through its leading end and then rejoining the leading ends, e.g., the last centimeter or so of the two split-leader sections, together). This feature can render it unnecessary to position (e.g., superimpose) a leading end of each of two split-leader sections on collection spool 90 in order to thread the split-leader sections so as to properly establish web-separation point 33 at initial position 34. That is, leading end 72 of leader portion 71 may merely be secured to collection spool 90, split sections 74 and 75 of leader portion 71 then positioned in their respective paths, and web-separation point 33 will be established at its desired initial position 34.

However provided (e.g., by way of the user manually splitting leader portion 71, or by way of pre-split sections 74 and 75 provided in leader portion 71), in such embodiments initial web-separation point 33 may be established at initial position 34 by unsplit trailing end 73 of leader portion 71 (which, in the case of a pre-split leader with sections 74 and 75, marks the trailing location at which sections 74 and 75 rejoin each other. If desired, trailing end 73 may be marked with indicia, reinforced, etc., in order to reduce the likelihood of a user accidentally tearing/splitting web 70 further (along the trailing direction of web 70) than desired in the act of loading the web into dispenser 1.

Device 80 may comprise any device which is desired to be dispensed in the manner described herein. Device 80 may be a personal safety protection device. In some embodiments, device 80 is a hearing protection device. In specific embodiments, device 80 is an earplug and/or a pair of corded earplugs (which in combination may be considered to be a single device). Exemplary earplugs include e.g. roll-down foam earplugs, such as the product available from Aearo Company, Indianapolis, Ind., under the trade designation E-A-R Classic; push-in foam earplugs, such as the product available from Aearo under the trade designation Aearo Push-in; and pre-molded reusable earplugs, such as the product available from Aearo under the trade designation E-A-R Ultrafit. In other embodiments, device 80 may comprise a semi-aural banded hearing protector such as the product available from Aearo under the trade designation CABOFLEX, or a hearing protective earmuff such as the product available from Aearo under the trade designation E-A-R Muffs. In still other embodiments, devices 80 may comprise safety eyewear such as safety glasses and/or goggles and the like; or may comprise skin protective devices such as facepieces, face shields, gloves, and the like; or may comprise personal respiratory protective devices such as respirators (e.g., flat-fold respirators, molded respirators, etc.); particulate masks such as those used to filter dust and pollen; medical and surgical masks, and the like. Some overlap exists between these categories, of course.

In preparing dispenser 1 for use, a cartridge 60 may be loaded into dispenser 1 (e.g., after removal of front cover 11 or by any other suitable way of accessing the interior of dispenser 1). A leader portion 71 of packaging web 70 is removed from cartridge 60 and is threaded through packaging web path 30 (e.g., past packaging web guiding vanes 32 and 36 and over packaging web guiding roller 31). The leader portion is then manually separated into first and second waste web leader portions. First waste web 44 leader is then threaded through first waste web path 40 (e.g., past first waste web guiding vane 41 and over first waste web guiding roller 42). Second waste web 54 leader is then threaded through second waste web path 50 (e.g., past first waste web guiding vane 51 and over first waste web guiding roller 52). The first and second waste web leaders are brought to collection spool 90, are placed in substantially overlapping relation, and are secured to collection spool 90. This may be done for example by inserting the overlapping web leaders through the slot between holding rod 95 and collection spool core 91, and rotating the collection spool sufficiently to pin the web leaders against the core to hold them sufficiently securely that continued rotation of collection spool 90 causes additional lengths of waste webs 44 and 54 to be co-wound onto collection spool 90. However, any suitable method of securing one or both waste web leaders to collection spool 90 may be used. These may include e.g. securing one or both leaders to core 91 with adhesive tape, manually wrapping one or both leaders around core 91 a sufficient number of times to sufficiently pin the web leaders against the core, and so on.

If packaging web 70 is of the general type shown in FIG. 8, leader portion 71 may be provided pre-split into sections 74 and 75 which may serve as leaders for first and second waste webs 44 and 54 respectively. In this case, leader portion 71 may be threaded through packaging web path 30, leading end 72 of leader portion 71 may be secured to collection spool 90, and then pre-split sections 74 and 75 may be positioned into waste web paths 40 and 50, respectively.

After the loading of cartridge 60 and the threading of the webs into their respective paths, (and with front cover 11 inserted into place), dispenser 1 is ready for use. Actuation of handle 111, handle 116, or both, will motivate rotation of collection spool 90, which causes the waste webs and the packaging web to move along their respective web paths as described previously, and causes additional packaging web to be drawn from cartridge 60. Actuation may continue until the leader portion of packaging web 70 has been drawn through the web paths to the point that the device-containing portion of packaging web 70 reaches the web-separation point and a device 80 is liberated. Actuation may continue uninterrupted if it is desired to dispense one or more additional devices 80. If not, dispenser 1 may be left as is until such time as it is desired to dispense one or more additional devices 80. Thus, use of dispenser 1 may, at various times, involve intermittent actuation, or continuous actuation. As mentioned previously, in some embodiments packaging web 70 may be loaded into dispenser 1 such that web-separation point 33 is initially located proximate one edge of opening 22 of device receptacle 20, with continued use of dispenser 1 causing web-separation point 33 to laterally traverse over at least a portion of opening 22.

With continued use of dispenser 1, the amount of packaging web 70 and devices 80 contained therein will gradually decrease. The amount remaining can be visually ascertained through aligned openings 12 and 62 as mentioned previously. Upon exhaustion of the entirety of packaging web 70, dispenser 1 can be opened (e.g., by removing front cover 11) and empty cartridge 60 removed therefrom. At least one flange can be removed from collection spool 90 and co-wound waste roll 77 can be slidably removed therefrom (e.g. as facilitated by the loosening or removal of holding rod 95, as described previously). Waste roll 77 can then be disposed or recycled, and collection spool 90 can be returned to its previous state. A fresh cartridge 60 can be inserted into dispenser 1 (or, cartridge 60 can be refilled with a fresh length of packaging web 70) and a fresh packaging web 70 threaded into place as described above.

In some embodiments, dispenser 1 may comprise a blade (which term encompasses any suitable sharp-edged tool) that may assist in separating (splitting) packaging web 70 into waste webs 44 and 54. In other embodiments, dispenser 1 may use self-sustaining web splitting (separation). This means that, once a portion of packaging web 70 is separated into waste webs 44 and 54 (e.g., in the loading and threading of the various web portions into their respective web paths as described above), upon motivating the webs to move along their respective paths, the web-splitting propagates along the longitudinal axis of packaging web 70 (for example, along an aforementioned line of weakness) without the use of any kind of blade. Thus, upon continued operation of dispenser 1, most or all of the entire length of packaging web 70 may be split into waste webs 44 and 54, without the use of any kind of blade.

Dispenser 1 as disclosed herein advantageously allows devices to be dispensed to a user without requiring the user to open packaging or to dispose of spent packaging. Dispenser 1 may be made of e.g. molded plastic, except for such particular components in which metal may be advantageously used. A locking mechanism may be used (e.g., on front cover 11) to prevent access to the interior of dispenser 1 if desired. Dispenser 1 may be used in a wall-mount configuration e.g. with back side 19 against a wall or other vertical surface; or may be used in a table-top configuration e.g. with bottom 27 resting on a horizontal surface. In a table-top configuration, a support stand may be used if desired.

LIST OF EXEMPLARY EMBODIMENTS

Embodiment 1

A dispenser configured to liberate at least one packaged device from a packaging web that is separable into first and second waste webs and that contains a plurality of packaged devices, the dispenser comprising: a packaging web path along which the packaging web is conveyed to a web-separation point at which the packaging web is separated into first and second waste webs with at least one device being liberated from the packaging web by the act of separating the packaging web into first and second waste webs; a device receptacle configured to receive the liberated device; a first waste web path along which the first waste web is conveyed to a collection spool; and, a second waste web path along which the second waste web is conveyed to the collection spool; the collection spool being configured so that the first and second waste webs can be co-wound on the collection spool to form a co-wound waste roll.

Embodiment 2

The dispenser of embodiment 1 wherein the web-separation point is a floating web-separation point.

Embodiment 3

The dispenser of any of embodiments 1 or 2 wherein the floating web-separation point is a traveling web-separation point.

Embodiment 4

The dispenser of any of embodiments 1 to 3 wherein the device receptacle comprises an opening comprising a lateral length and through which the liberated device can enter the device receptacle, wherein the web-separation point is located vertically above some portion of the lateral length of the opening of the device receptacle, and wherein in the course of continued or successive operation of the dispenser the web-separation point traverses at least a portion of the lateral length of the opening of the device receptacle.

Embodiment 5

The dispenser of any of embodiments 1 to 4 wherein the first waste web path is at least partially defined by a first waste web guiding vane that is located laterally outward of the device receptacle and that comprises a laterally outward-facing surface configured to allow the first waste web to slidably traverse at least a portion of the outward-facing surface; and wherein the second waste web path is at least partially defined by a second waste web guiding vane that is located laterally outward of the device receptacle and that comprises a laterally outward-facing surface configured to allow the second waste web to slidably traverse at least a portion of the outward-facing surface of the second waste web guiding vane.

Embodiment 6

The dispenser of embodiment 5 wherein the first and second waste web guiding vanes are first and second generally arcuate side portions of the device receptacle.

Embodiment 7

The dispenser of any of embodiments 5 to 6 wherein the first waste web path is further defined by a first waste web guiding roller that is positioned in the first waste web path between the first waste web guiding vane and the collection spool, and wherein the second waste web path is further defined by a second waste web guiding roller that is positioned in the second waste web path between the second waste web guiding roller and the collection spool.

Embodiment 8

The dispenser of any of embodiments 1 to 7 wherein the packaging web path is at least partially defined by a packaging web guiding roller that is positioned vertically above some portion of the device receptacle.

Embodiment 9

The dispenser of any of embodiments 1 to 8 wherein the packaging web path is at least partially defined by at least one packaging web guiding vane a laterally outward-facing surface of which is configured to allow the packaging web to slidably traverse at least a portion of the outward-facing surface of the packaging web guiding vane, with at least a portion of the packaging web guiding vane being configured to prevent contact between at least a portion of the packaging web and at least a portion of a waste web.

Embodiment 10

The dispenser of any of embodiments 1 to 9 wherein the dispenser comprises a housing and further comprises a drivetrain that is connected to at least one actuator located outside of the dispenser housing and that is configured to motivate the collection spool to rotate so as to motivate movement of the packaging web and the first and second waste webs.

Embodiment 11

The dispenser of embodiment 10 wherein the dispenser housing comprises a first major side comprising an opening through which liberated devices may be removed from the device receptacle, and first and second minor sides that laterally flank the first major side, and wherein the actuator is positioned laterally outwardly adjacent a minor side of the dispenser.

Embodiment 12

The dispenser of any of embodiments 1 to 11 wherein the dispenser comprises a housing and wherein the packaging web is provided in a cartridge comprising a first opening through which the packaging web can exit the cartridge and enter the packaging web path, and a second opening through which the amount of packaging web remaining in the cartridge can be observed through a transparent portion of the dispenser housing that is aligned with the second opening of the cartridge.

Embodiment 13

The dispenser of any of embodiments 1 to 12 wherein the collection spool is configured so that the co-wound waste roll can be removed from the collection spool by sliding the co-wound waste roll in a direction generally aligned with the longitudinal axis of the collection spool.

Embodiment 14

The dispenser of embodiment 13 wherein the collection spool comprises a holding rod configured to retain leader portions of the first and second waste webs on the collection spool and that can be detached from the spool, or moved in relation to the spool, in order to facilitate removal of the co-wound webs, and wherein the collection spool further comprises at least one flange that can be removed in order to facilitate removal of the co-wound webs.

Embodiment 15

The dispenser of embodiment 14 wherein the holding rod can be detached from the collection spool by being moved in a direction generally aligned with the spool axis, or can be moved in a radially inward direction relative to the collection spool.

Embodiment 16

The dispenser of any of embodiments 1 to 15 wherein the devices are protective earplugs.

Embodiment 17

The dispenser of any of embodiments 1 to 16 wherein the packaging web comprises a leader portion that does not contain devices and that is at least as long as the length of the first waste web path.

Embodiment 18

The dispenser of embodiment 17 wherein the leader portion comprises a longitudinal length along which the leader portion is split into two sections, and comprises an unsplit leading end and an unsplit trailing end.

Embodiment 19

A method of liberating at least one packaged device from a packaging web that is separable into first and second waste webs and that contains a plurality of packaged devices, the method comprising: conveying the packaging web along a packaging web path to a web-separation point at which the packaging web is separated into first and second waste webs with at least one device being liberated from the packaging web by the act of separating the packaging web into first and second waste webs; allowing the liberated device to fall into a device receptacle from which it may be retrieved by a user; conveying the first waste web along a first waste web path to a collection spool; conveying the second waste web along a second waste web path to the collection spool; and, co-winding the first and second waste webs on the collection spool.

Embodiment 20

The method of embodiment 19 wherein at the web-separation point the first waste web is motivated to move generally in a first direction, and the second waste web is motivated to move in a second direction that is generally opposite that of the first waste web, so that separating the packaging web into first and second waste webs causes the device to be liberated from the packaging web and to fall in a direction substantially orthogonal to the directions of motion of the first and second waste webs at the web-separation point, into the device receptacle.

Embodiment 21

The method of any of embodiments 19 to 20 wherein the conveying of the webs is motivated by an actuator, wherein the devices are spaced along the elongated length of the packaging web, and wherein continued or successive actuation of the actuator causes multiple devices to be successively liberated from the packaging web and causes continuous lengths of the first and second waste webs to be co-wound onto the collection spool.

Embodiment 22

The method of any of embodiments 19 to 21 wherein the web-separation point is located vertically above some portion of a lateral length of an opening of the device receptacle, and wherein in the course of continued or successive performing of the method the web-separation point traverses over at least a portion of the lateral length of the opening of the device receptacle.

Embodiment 23

The method of any of embodiments 19 to 22, wherein the method uses a dispenser comprising any of embodiments 1-17.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather extends at least to the structures described by the language of the claims, and the equivalents of those structures. To the extent that there is a conflict or discrepancy between this specification and the disclosure in any document incorporated by reference herein, this specification will control.

What is claimed is:

1. A dispenser configured to liberate at least one packaged device from a packaging web that is separable into first and second waste webs and that contains a plurality of packaged devices, the dispenser comprising:
   a packaging web path along which the packaging web is conveyed to a web-separation point at which the packaging web is separated into first and second waste webs with at least one device being liberated from the packaging web by the act of separating the packaging web into first and second waste webs;
   a device receptacle configured to receive the liberated device;
   a first waste web path along which the first waste web is conveyed to a collection spool;
   and,
   a second waste web path along which the second waste web is conveyed to the collection spool;
   the collection spool being configured so that the first and second waste webs can be co-wound on the collection spool to form a co-wound waste roll,
   wherein the device receptacle comprises an opening comprising a lateral length and through which the liberated device can enter the device receptacle, wherein the web-separation point is a floating, traveling web-separation point that is located vertically above some portion of the lateral length of the opening of the device receptacle, and wherein in the course of continued or successive operation of the dispenser the web-separation point traverses at least a portion of the lateral length of the opening of the device receptacle.

2. The dispenser of claim 1 wherein the first waste web path is at least partially defined by a first waste web guiding vane that is located laterally outward of the device receptacle and that comprises a laterally outward-facing surface configured to allow the first waste web to slidably traverse at least a portion of the outward-facing surface; and wherein the second waste web path is at least partially defined by a second waste web guiding vane that is located laterally outward of the device receptacle and that comprises a laterally outward-facing surface configured to allow the second waste web to slidably traverse at least a portion of the outward-facing surface of the second waste web guiding vane.

3. The dispenser of claim 2 wherein the first and second waste web guiding vanes are first and second generally arcuate side portions of the device receptacle.

4. The dispenser of claim 2 wherein the first waste web path is further defined by a first waste web guiding roller that is positioned in the first waste web path between the first waste web guiding vane and the collection spool, and wherein the second waste web path is further defined by a second waste web guiding roller that is positioned in the second waste web path between the second waste web guiding roller and the collection spool.

5. The dispenser of claim 1 wherein the packaging web path is at least partially defined by a packaging web guiding roller that is positioned vertically above some portion of the device receptacle.

6. The dispenser of claim 1 wherein the packaging web path is at least partially defined by at least one packaging web guiding vane a laterally outward-facing surface of which is configured to allow the packaging web to slidably traverse at least a portion of the outward-facing surface of the packaging web guiding vane, with at least a portion of the packaging web guiding vane being configured to prevent contact between at least a portion of the packaging web and at least a portion of a waste web.

7. The dispenser of claim 1 wherein the dispenser comprises a housing and further comprises a drivetrain that is connected to at least one actuator located outside of the dispenser housing and that is configured to motivate the collection spool to rotate so as to motivate movement of the packaging web and the first and second waste webs.

8. The dispenser of claim 7 wherein the dispenser housing comprises a first major side comprising an opening through which liberated devices may be removed from the device receptacle, and first and second minor sides that laterally flank the first major side, and wherein the actuator is positioned laterally outwardly adjacent a minor side of the dispenser.

9. The dispenser of claim 1 wherein the collection spool is configured so that the co-wound waste roll can be removed from the collection spool by sliding the co-wound waste roll in a direction generally aligned with the longitudinal axis of the collection spool.

10. The dispenser of claim 9 wherein the collection spool comprises a holding rod configured to retain leader portions of the first and second waste webs on the collection spool and that can be detached from the spool, or moved in relation to the spool, in order to facilitate removal of the co-wound webs, and wherein the collection spool further comprises at least one flange that can be removed in order to facilitate removal of the co-wound webs.

11. The dispenser of claim 10 wherein the holding rod can be detached from the collection spool by being moved in a direction generally aligned with the spool axis, or can be moved in a radially inward direction relative to the collection spool.

12. The dispenser of claim 1 wherein the devices are protective earplugs.

13. The dispenser of claim 1 wherein the packaging web comprises a leader portion that does not contain devices and that is at least as long as the length of the first waste web path.

14. The dispenser of claim 13 wherein the leader portion comprises a longitudinal length along which the leader portion is split into two sections, and comprises an unsplit leading end and an unsplit trailing end.

15. A dispenser configured to liberate at least one packaged device from a packaging web that is separable into first and second waste webs and that contains a plurality of packaged devices, the dispenser comprising:
  a packaging web path along which the packaging web is conveyed to a web-separation point at which the packaging web is separated into first and second waste webs with at least one device being liberated from the packaging web by the act of separating the packaging web into first and second waste webs;
  a device receptacle configured to receive the liberated device;
  a first waste web path along which the first waste web is conveyed to a collection spool;
  and,
  a second waste web path along which the second waste web is conveyed to the collection spool;
  the collection spool being configured so that the first and second waste webs can be co-wound on the collection spool to form a co-wound waste roll;
  wherein the dispenser comprises a housing and wherein the packaging web is provided in a cartridge comprising a first opening through which the packaging web can exit the cartridge and enter the packaging web path, and a second opening through which the amount of packaging web remaining in the cartridge can be observed through a transparent portion of the dispenser housing that is aligned with the second opening of the cartridge, and
  wherein the device receptacle comprises an opening comprising a lateral length and through which the liberated device can enter the device receptacle, wherein the web-separation point is a floating, traveling web-separation point that is located vertically above some portion of the lateral length of the opening of the device receptacle, and wherein in the course of continued or successive operation of the dispenser the web-separation point traverses at least a portion of the lateral length of the opening of the device receptacle.

16. The dispenser of claim 15 wherein the first waste web path is at least partially defined by a first waste web guiding vane that is located laterally outward of the device receptacle and that comprises a laterally outward-facing surface configured to allow the first waste web to slidably traverse at least a portion of the outward-facing surface; and wherein the second waste web path is at least partially defined by a second waste web guiding vane that is located laterally outward of the device receptacle and that comprises a laterally outward-facing surface configured to allow the second waste web to slidably traverse at least a portion of the outward-facing surface of the second waste web guiding vane.

17. The dispenser of claim 16 wherein the first and second waste web guiding vanes are first and second generally arcuate side portions of the device receptacle.

18. The dispenser of claim 16 wherein the first waste web path is further defined by a first waste web guiding roller that is positioned in the first waste web path between the first waste web guiding vane and the collection spool, and wherein the second waste web path is further defined by a second waste web guiding roller that is positioned in the second waste web path between the second waste web guiding roller and the collection spool.

19. The dispenser of claim 15 wherein the packaging web path is at least partially defined by a packaging web guiding roller that is positioned vertically above some portion of the device receptacle.

20. The dispenser of claim 15 wherein the packaging web path is at least partially defined by at least one packaging web guiding vane a laterally outward-facing surface of which is configured to allow the packaging web to slidably traverse at least a portion of the outward-facing surface of the packaging web guiding vane, with at least a portion of the packaging web guiding vane being configured to prevent contact between at least a portion of the packaging web and at least a portion of a waste web.

21. The dispenser of claim 15 wherein the dispenser comprises a housing and further comprises a drivetrain that is connected to at least one actuator located outside of the dispenser housing and that is configured to motivate the collection spool to rotate so as to motivate movement of the packaging web and the first and second waste webs.

22. The dispenser of claim 21 wherein the dispenser housing comprises a first major side comprising an opening through which liberated devices may be removed from the device receptacle, and first and second minor sides that laterally flank the first major side, and wherein the actuator is positioned laterally outwardly adjacent a minor side of the dispenser.

23. The dispenser of claim 15 wherein the collection spool is configured so that the co-wound waste roll can be removed from the collection spool by sliding the co-wound waste roll in a direction generally aligned with the longitudinal axis of the collection spool.

24. The dispenser of claim 23 wherein the collection spool comprises a holding rod configured to retain leader portions of the first and second waste webs on the collection spool and that can be detached from the spool, or moved in relation to the spool, in order to facilitate removal of the co-wound webs, and wherein the collection spool further comprises at least one flange that can be removed in order to facilitate removal of the co-wound webs.

25. The dispenser of claim 24 wherein the holding rod can be detached from the collection spool by being moved in a direction generally aligned with the spool axis, or can be moved in a radially inward direction relative to the collection spool.

26. The dispenser of claim 15 wherein the devices are protective earplugs.

27. The dispenser of claim 15 wherein the packaging web comprises a leader portion that does not contain devices and that is at least as long as the length of the first waste web path.

28. The dispenser of claim 27 wherein the leader portion comprises a longitudinal length along which the leader portion is split into two sections, and comprises an unsplit leading end and an unsplit trailing end.

* * * * *

UNITED STATES PATENT AND TRADEMARK OFFICE
CERTIFICATE OF CORRECTION

PATENT NO. : 8,528,779 B2  Page 1 of 1
APPLICATION NO. : 12/913417
DATED : September 10, 2013
INVENTOR(S) : Jeffrey Lee Hamer It is certified that error appears in the above-identified patent and that said Letters Patent is hereby corrected as shown below:

Title Page – Column 2 (Assistant Examiner)
Line 1, Delete "Kevin" and insert -- Kelvin --, therefor.

In the Specifications
Column 4
Line 46, Delete "thereof" and insert -- thereof. --, therefor.

Signed and Sealed this
Eighteenth Day of March, 2014

Michelle K. Lee
*Deputy Director of the United States Patent and Trademark Office*